United States Patent [19]

Swirska et al.

[11] Patent Number: 5,643,907

[45] Date of Patent: Jul. 1, 1997

[54] PHARMACEUTICAL COMPOSITION CONTAINING 5-MORPHOLINOMETHYL-3-(4-CHLOROBENZYLIDENEAMINE)-2-OXAZOLIDINONE AND ITS USE FOR THE TREATMENT OF CNS DISORDERS

[75] Inventors: Alicja Swirska, Jablonna; Leszek Krzywosinski, Warsaw; Maria Bogdal, Warsaw; Marta Serwin-Krajewska, Warsaw; Maria Kobylinska, Warsaw; Andrzej Grzeszkiewicz, Warsaw, all of Poland

[73] Assignee: Instytut Farmaceutiyczny, Warsaw, Poland

[21] Appl. No.: 495,428

[22] PCT Filed: Jan. 24, 1994

[86] PCT No.: PCT/PL94/00004

§ 371 Date: Jul. 26, 1995

§ 102(e) Date: Jul. 26, 1995

[87] PCT Pub. No.: WO94/16705

PCT Pub. Date: Aug. 4, 1994

[30] Foreign Application Priority Data

Jan. 27, 1993 [PL] Poland ............... 297-548

[51] Int. Cl.⁶ .................. A61K 31/535
[52] U.S. Cl. .................. 514/236.8
[58] Field of Search .................. 514/236.8

[56] References Cited

U.S. PATENT DOCUMENTS 5,232,931  8/1993  Prucher .................. 514/321

FOREIGN PATENT DOCUMENTS

| 0459256 | 5/1990 | European Pat. Off. . |
| 4005371 | 2/1991 | Germany . |
| 2078882 | 12/1975 | Japan . |
| 2078884 | 12/1975 | Japan . |
| 5207888 | 12/1975 | Japan . |

OTHER PUBLICATIONS

Swirska, A. 'Hypotensive derivatives of . . . ' Chemical Abstracts, vol. 60, No. 4, (1964), Columbus, Ohio, US; abstract No. 4137.

Acta Polon. Pharm., vol. 19, No. 4, (1962), pp. 317–324.

Kessler, H.–J., et al., 'Chemotherapeutische Nitro–heterocyclen XXI . . . ' Eur. J. Med. Chem. vol. 11, No. 1, 1976, pp. 19–23.

Alicja Swirska, "5-Morpholinomethylo-3-Amino-2-oxazolidone Derivatives with Hypotensive Activity," Acta Polon. Pharm., vol. 19, No. 4, 1962: 317–324.

Patent Abstracts of Japan, vol. 1, No. 120 (C-77) (2765) 12 Oct. 1977 & JP,A,52 078 881 (Sumitomo Kagaku Kogyo K.K.) 7 Feb. 1977.

*Primary Examiner*—Raymond Henley, III
*Attorney, Agent, or Firm*—Ladas & Parry

[57] ABSTRACT

A method of treating central nervous system diseases and disorders, the diseases and disorders being responsive to drugs possessing psychotropic activity. The method involves administering to a subject suffering from the disease or disorder a therapeutically effective amount of 5-morpholinomethyl-3-(4-chlorobenzylideneamine)-2-oxazolidinone or a pharmaceutically acceptable salt of 5-morpholinomethyl-3-(4-chlorobenzylideneamine)-2-oxazolidinone. The invention also relates to a pharmaceutical composition, the composition having pharmaceutically acceptable carriers and 5-morpholinomethyl-3-(4-chlorobenzylideneamine)-2-oxazolidinone and/or a pharmaceutically acceptable salt of 5-morpholinomethyl-3-(4-chlorobenzylideneamine)-2-oxazolidinone.

24 Claims, No Drawings

PHARMACEUTICAL COMPOSITION CONTAINING 5-MORPHOLINOMETHYL-3-(4-CHLOROBENZYLIDENEAMINE)-2-OXAZOLIDINONE AND ITS USE FOR THE TREATMENT OF CNS DISORDERS

This application is A-371 of PCT/PL94/00004 filed Jan. 24, 1994.

The present invention relates to the pharmaceutical composition, posessing psychotropic and especially anti-depressive activity, which can be used in the treatment of the central nervous system diseases and its functional disorders.

Psychotropic drugs known for their effects on the central nervous system are applicable in the therapy of psychical disorders and as assisting drugs in the treatment of other systems. According to their application the psychotropic drugs fall into five classes: neuroleptics, tranquilisers, anxiolytics, anti-depressants and nootropics. Depression affects in a varying degree ca 6% of the population. It is the result of interaction between the negative factors of the environment (stress) and the individual biochemical susceptibility, which is genetically conditioned. The biochemical basis for depression is related to the abnormal level of monoamines in the brain, particularly noradrenaline and serotonin (5-hydroxytryptamine). Hence the therapy of depression is focused on the question of increasing the level of monoamines in the brain. Very frequently applied in the therapy of depression are tri- and tetracyclic drugs. They produce an effect on wide range of neurotransmitters, including noradrenaline, serotonin, dopamine, histamine and acetylocholine. However, these drugs, due to their multidirectional action, have a number of side effects and can also cause an addiction. In the therapy of depression noncompetitive monoamine oxidase (MAO) inhibitors have been applied as well. MAO inhibitors, however, cause some metabolism disturbances of monoamines taken with food. This is why their application is reduced to the cases which do not react to other drugs.

The significant progress was the introduction of new serotonin re-uptake inhibitors. Their characteristic feature is high effectiveness and a smaller number of side effects. The chemical structure of these drugs considerably differs from the classical tri- and tetracyclic anti-depressants.

New drugs with anti-depressive effect have been searched in different chemical classes.

In the patent application number DE 4005371 the derivatives of N-aryl-2-piperidinoethyl-2-oxazolidinone and the pharmaceutical compositions containing them were disclosed. It was stated that those agents showed the effect on the central nervous system, particularly sedative, tranqulising, neuroleptic and anti-depressive effects.

The derivatives of 3-aryl-4-piperidinoalkil-2-oxazolidinone and pharmaceutical compositions containing them are known from the european patent application number EP 459256. They show central nervous system activity, particularly sedative, tranquilising, neuroleptic and anti-depressive activity.

According to the invention there is provided a pharmaceutical composition, which contains as the active substance 5-morpholinomethyl-3-(4-chlorobenzylideneamine)-2-oxazolidinone of formula I

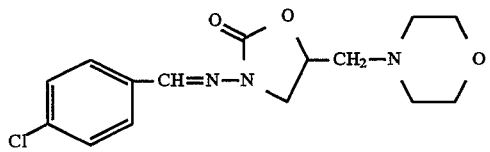

and/or pharmaceutically acceptable salt thereof and a pharmaceutically acceptable carrier and optionally at least one auxilliary substance.

The pharmaceutical composition according to the invention contains an active substance in its free form or in the form of pharmaceutically acceptable salt, particularly acid addition salt. These can be salts with inorganic acids, such as hydrochloric, hydrobromic, phosphoric acid and organic acids, such as for example formic, acetic, propionic, malonic, citric, lactic, tartaric, gluconic, nicotinic, methane—or ethanesulphonic, ascorbic, naphthalenesulphonic and fumaric acid.

In the preferred embodiment the pharmaceutical composition according to the invention contains as the active substance 5-morpholinomethyl-3-(4-chlorobenzylideneamine)-2-oxazolidinone hydrochloride.

A further aspect the present invention relates to the use of 5-morpholinomethyl-3-(4-chlorobenzylideneamine)-2-oxazolidinone of formula I given above or pharmaceutically acceptable salt thereof for the preparation of a medicament having central nervous system activity.

Another aspect the present invention relates to the method of treatment of central nervous system diseases and disorders which comprises the administration to a person suffering from such disease or disorder a therapeutically effective amount of 5-morpholinomethyl-3-(4-chlorobenzylideneamine)-2-oxazolidinone of formula I given above and or pharmaceutically acceptable salt thereof.

The daily dosage of the 5-morpholinomethyl-3-(4-chlorobenzylideneamine)-2-oxazolidinone applied for the therapy of the central nervous system, especially depression, ranges between 1 to 10 mg/kg body weight and depends on the mode of administration.

5-Morpholinomethyl-3-(4-chlorobenzylideneamine)-2-oxazolidinone can be obtained by the condensation of 5-morpholinomethyl-3-amine-2-oxazolidinone with 4-chlorobenzaldehyde in water-alcohol solution and acidic environment (pH 5–6), as described by A. Swirska in Acta Polon. Pharm. 19, 3/7, 324, 1962. Acid addition salts can be obtained by conventional methods, well known to a person skilled in the art.

The compositions according to the invention may be in any form of dosage units known in the pharmaceutical practice, for instance as described in *Remington's Pharmaceutical Sciences*, 18th edition, Mac Publishing Co., 1990. It can be the form for oral administration, for example tablet, capsule, powder, granules, syrup, parenteral form, such as sterile solution or emulsion, for example water or oil solution and emulsion for injections or infusions, or freeze-dried powder for reconstitution ex tempore. They can also have form of suppositories for rectal administration.

The compositions may contain conventional organic or inorganic carriers, typically used in pharmaceutical technology, chosen depending on the required form of the composition. Suitable carriers include for instance water, vegetable oils, benzyl alcohol, polyethylene glycol, gelatine, carbohydrates, such as for instance starch and starch derivatives, cellulose and cellulose derivatives, lactose, magnesium stearate, talc, etc.

The Compositions according to the invention can contain auxiliary substances such as for example preservatives, stabilizers, buffers, emulsifiers, solubilizers, salts regulating osmotic pressure, binders, lubricants, glidants, disintegrants, coloring agents, flavoring agents, all of them applied according to the form and need.

Solid oral forms can be obtained by procedures well-known from pharmaceutical practice. For instance tablets can be made either by means of conventional methods of mixing and direct compressing into tablets or tabletting with preceding granulation. Tablets can be covered with parenteral coating, resistant against the action of gastric juice or regulating the absorption time of active substance.

Liquid oral forms can be obtained by dissolving or suspending the active substance in water or other solvents toghether with conventional auxiliary agents, for instance flavours. Such preparations can be also in dry form which is dissolved directly before use.

Forms for parenteral administration are produced from the active substance and sterile vehiculum. The solutions are obtained by dissolving the active substance in liquid medium, sterile filtration and sealing. Auxiliary substances also can be dissolved in the liquid medium. For prolonging the preparation stability the mixture in the ampoule can be freeze-dried. The suspensions for parenteral administration are obtained generally in the same way. However, the active substance instead of being dissolved is suspended in a liquid carrier. Additional agents for keeping the active substance homogenous are possible. In that case sterilisation is not obtained through the process of filtration.

The results of pharmacological examinations:

Materials and methods:

The experiments were conducted on mice, both sexes, of the Balb/c and outbred Ipf:M/2 strain (20–40 g), male rats of the Wistar and outbred Ipf:R/2 strain (160–240 g). The preparations were administered per os (p.o.) in the form of 5% carboxymethylcellulose suspension or intraperitoneally (i.p.) in the form of water solutions and steady volumes: mice 0,1 ml/10 g i.p. or 0,2 ml/10 g p.p.; rats 0,2 ml/100 g i.p. or p.o.. Control animals were given a solvent in the corresponding way. The statistic evaluation of the results was made by means of t-Student test.

1) The influence on the rats behaviour in "despair test".

The experiment was conducted according to the method described by Porsolt in Eur. J. Pharmacol., 1978, 47, 379. The rats were placed separately in upright, metallic cylindrical containers, 60 cm high and 18 cm in diameter, containing 15 centimeters of water, at a temperature of 25° C. After 15 minutes the animals were taken from the containers, dried and put into cages. After 24 hours the rats were dived in water again and for 5 minutes the complete immobility period was measured. The examined preparation (containing 5-morpholinomethyl- 3-(4-chlorobenzylideneamine)-2-oxazolidinone hydrochloride) or imipramine (IMI) was administered per os twice: at 24 hours and one hour before the beginning of the observation. The result is presented in Table 1.

TABLE 1

The effect on the rats behaviour in "despair test"

| Administered prevaration (mg/kg) | The immobility period in sec./5 minutes | |
|---|---|---|
| | mean ± SE | % |
| — | 273 ± 5, 3 | 100 |
| Examined preparation 40 | 245 ± 14, 4 | 89 |
| Examined preparation 200 | 225 ± 14, 5* | 82 |
| IMI 20 | 240 ± 5, 0* | 88 |

The number of animals in the group = 8
*p < 0, 01

The examined preparation administered in the dosage of 200 mg/kg shortened the rats' immobility period by 18% in relation to the control group. The effect equals approximately to the effect of IMI (20 mg/kg) applied in the similar way.

2) The intensification of L-Dopa effects in reserpine pretreated mice.

The examined preparation was administered to mice p.o. in the dosages of 40 and 200 mg/kg 17 hours after reserpine in the dosage of 2,5 mg/kg had been administered intraperitoneally. After one hour L-dopa was injected in the dosage of 300 mg/kg. The intensification of L-dopa anti-reserpine action was evaluated according to the following parameters of the animals behaviour: mobility, irritability, ptosis and body temperature. According to the same empirical system IMI was examined in the dosages of 8 and 40 mg/kg. The results are presented in Table 2.

TABLE 2

The intensification of L-dopa effects in reserpine pretreated mice.

| Preparation | Dosage (mg/kg) | Ptosis | | | | | Temper. | | Mobility | Irritability |
|---|---|---|---|---|---|---|---|---|---|---|
| | | 30' | 60' | 90' | 120' | 180' | 60' | 120 | | |
| Control | — | 4, 0 | 4, 0 | 4, 0 | 4, 0 | 4, 0 | 29, 1 | 30, 1 | Reduced mobility | None |
| Control + L-Dopa | — | 3, 7 | 3, 5 | 3, 0 | 3, 3 | 4, 0 | 29, 3 | 30, 3 | Temporal translocations, no distinct incitement of mobility | Little |
| Examined preparation + L-Dopa | 40 | 1, 8 | 1, 3 | 1, 5 | 3, 5 | 3, 9 | 34, 5 | 32, 8 | Translocations, running, squeaks, jumping, lasting till 90' | Very strong irritability to impulses to 90' |
| Examined preparation + L-Dopa | 200 | 2, 0 | 2, 0 | 2, 5 | 2, 1 | 3, 4 | 30, 0 | 34, 7 | No body posture, reflex till 60', very strong incitement of mobility, squeaks, jumpings till 120' | No irritability till ca 60'; afterwards very strong till 120' |
| IMI + L-Dopa | 8 | 1, 4 | 1, 8 | 1, 1 | 2, 4 | 3, 9 | 34,3 | 32, 3 | Translocations, running, squeaks till 120' | Very strong irritability till 90' |
| IMI + L-Dopa | 40 | 2, 5 | 2, 3 | 1, 6 | 2, 4 | 4, 0 | 32, 2 | 31, 6 | Incitement of mobility, squeaks (lesser than after 8 mg/kg) | Quite strong irritability to impulses lasting till 90' |

It was found that the examined preparation intensified the behavioural effects of L-dopa action in reserpine pretreated mice in the same way as IMI. It reduced ptosis and hypothermy and raised the animals' mobility and irritability. A smaller dosage proved to be more effective than a bigger one. After 200 mg/kg had been applied, a distinct two-phase action of the examined preparation was observed. In the first hour after the application it came to the loss of body posture (righting) reflex. After 90 minutes there appeared irritability and big incitement, which lasted over an hour.

3) The intensification of L-dopa effects in mice premedicated with pargyline.

Three hours after the oral administration of pargyline in the dosage of 40 mg/kg, there was applied orally either the examined preparation or IMI, followed after one hour by L-dopa administered intraperitoneally in the dosage of 200 mg/kg. The behaviour of the mice was evaluated according to the following 5-level score:

1 - piloerection, Straub's tail, exophtalmos of eyes, minute salivating, irritability.

2 - as above + translocations, single jumps.

3 - as above + bigger incitement of mobility, frequent jumps, climbing, single squeaks.

4 - as above + great incitement of mobility, aggresion, fights.

5 - as above + maximum incitement of mobility and aggresion

The results are presented in Table 3.

TABLE 3

The intensification of L-dopa effects in mice premedicated with pargyline

| Preparation | Dosage mg/kg p.o. | Reaction of mice according to score |
|---|---|---|
| Control | — | 1–2 |
| Examined preparation | 10 | 5 |
|  | 20 | 5 |
|  | 40 | 5 |
|  | 200 | 3–4 |
| IMI | 4 | 4 |
|  | 40 | 3–4 |

The number of animals in the group = 8.

The examined preparation proved very strong intensification of L-dopa effects in mice premedicated with pargyline. The strongest mobility and emotion incitement was observed after the dosages of 10, 20 and 40 mg/kg. The examined preparation shows in this test stronger effectiveness than IMI.

4) The influence on the concentration of beta-adrenergic cerebral receptors in vivo.

Rats were administered the examined preparation in the form of intraperitoneally injection and the dosage of 200 mg/kg twice daily for six weeks. In the same empirical system IMI was examined in the dosage of 10 mg/kg. The animals were killed 24 hours after the last injection and their cerebral cortexes were skeletonized.

The population of the beta-adrenergic receptor was characterised by the examination of the parameters of the $^3$H-dihydroalprenolol ($^3$H-DHA) bonding to the membranes (fractiom $P_2$) of the cerebral cortex. The tissue was homogenised in 20 volumes of the 50 mM buffer TRIS-HCl, pH 7,6 in the Polytron disintegrator (position 4,155) and centrifuged at 1000 g for 10 minutes. The supernatant was decanted and again centrifuged at 25000 for 20 minutes. The operations were conducted in the temperature of 0°–4° C. The precipitate, after the second centrifugation, decanting and removing the supernatant, was kept in the temperature of −18° C. until the time of incubation (no longer than 48 hours). The final fraction $P_2$ was obtained by the subsequent process of the sediment homogenisation in such a volume of 50 mM buffer TRIS-HCl, pH 7,6, that the final concentration of protein amounted to 1,5 mg/ml.

The incubation mixture, containing 450 μl of the fraction $P_2$ suspension, 50 μl of the $^3$H-DHA solution (6 different solutions; the final concentrations in the mixture 0,05–3 mmol/litr) and 50 μl of buffer or propranolol solution (the final concentration in the sample 10 μl/litr) was incubated for 30 minutes in the temperature of 25° C. The incubation was finished by filtrating the suspension through filters made of glass fibres. The filters were twice rinsed with 5 ml of cold (0° C.) buffer TRIS-HCl, pH 7,6, and placed in scintillation minivessels, to which Bray's liquid was added. The radioactivity was measured by the Packard scintillation counter, model B329 with the efficiency of 36–37%.

The specific bonding was defined as the radioactivity difference between the samples incubated in the absence of propranolol (complete bonding) and in the presence of 10 μM of propranolol (blank). The data from the counter (dpm) were recalculated individually into the decay frequence (dpm), calculating it from the individual efficiency of each sample, received from the relation of impulses in the canals A and B. $B_{max}$ value and the constant of dissociation $K_D$ was calculated from the Scatchard diagrams, which were rectilinear. The results are presented in Table 4.

TABLE 4

The effect of the chronic administration of the examined preparation or IMI on the $^3$H-alprenolol bonding to the membranes of a rats' cerebral cortex.

| Prepar. daily dosage mg/kg | $N^1$ | $B_{max}$ fmole/mg protein X ± SEM | % | $K_D$ nmol/litre X ± SEM | % |
|---|---|---|---|---|---|
| Control | 29 | 134, 2 ± 111, 7 | 100 | 1, 94 ± 0, 24 | 100 |
| IMI | 23 | 80, 8 ± 8, 23 | 60 | 2, 05 ± 0, 28 | 129 |
| Examined preparation |  |  |  |  |  |
| 40 | 29 | 89, 4 6, 91 | 67 | 1, 23 0, 18 | 63 |
| 200 | 24 | 96, 4 7, 67 | 72 | 1, 31 0, 13 | 68 |
| F(df 3/101) |  | 7, 44 (p < 0, 0001) |  | 3, 84 (p < 0, 05) |  |

[1]total number of points (average number from two operations) used for fixing the $B_{max}$ and $K_D$ values. The X and SEM values were calculated by means of regression analysis.

The administration of the preparations caused a considerable decline of the concentration of beta-adrenergic receptors.

The effects of imipramine or both dosages of the examined preparation on the concentration of receptors did not differ considerably. As distinct from imipramine, the chronic administration of the examined preparation in both dosages caused a statistically considerable decline of the constant of dissociation value $K_D$ and consequently the increase of the beta-adrenergic receptor affinity.

5) The effect on the uptake of monoamines in vivo.

The point of reference for measuring the inhibiting effect on the uptake of noradrenaline was the protection from the effect of 6-hydroxydopamine (6-OHDA), which was administered intraventricularly. Rats were applied intraventricularly 250 μg of 6-OHDA in the volume of 20 μl of 0,9% solution of HCl and 0,1% solution of ascorbic acid. One hour before the 6-OHDA application the rats were administered IMI in the dosage of 20 mg/kg or the examined preparation in the dosages of 40 or 400 mg/kg. The animals were decapitated 7 days after and the level of noradrenaline in the whole brain was measured by the division on the Sephadex G-10 column and fluorimetric assay following oxidation. The results are presented in Table 5.

TABLE 5

The effect of the examined preparation and IMI on the uptake of noradrenaline in vivo.

| Group | Concentration of noradrenaline in the brain (mg/kg tissue) | |
|---|---|---|
| | X ± SEM | % in relation to the group after chemo-sympathectomy |
| Control | 205 ± 10, 5 (10) | 216 |
| 6-OHDA | 95 ± 6, 9 (10) | 100 |
| IMI, 20 before 6-OHDA | 179 ± 113, 5 (9) | 188 |
| Examined preparation | | |
| 200 before 6-OHDA | 148 ± 24, 9 (8) | 155 |
| 40, before 6-OHDA | 88 ± 14, 3 (10) | 92 |
| F (4/42 13, 55 ($p < 0,0001$) | | |

It was observed that 6-OHDA administered intraventricularly causes a considerable (over 50%) decline of the noradrenalin content in the cerebrum. A low dosage of the examined preparation does not prevent the effect of 6-OHDA completely. However, the higher dosage inhibits it almost as effectively as IMI. Concluding, the examined preparation, applied in high dosages, proves effective in inhibiting the uptake of noradrenaline.

The point of reference for measuring the inhibitory effect on the uptake of serotonin was the protection from the effect of intraperitoneally applied p-chloramphetamine. p-chloramphetamine in the dosage of 10 mg/kg was administered 60 minutes after citalopram in the dosage of 20 mg/kg or the examined preparation in the dosage of 400 mg/kg had been applied for confrontation. The animals were decapitated three hours later and the level of serotonin was measured by means of the same procedure as the level of noradrenalin. The results are presented in Table 6.

TABLE 6

The effect of examined preparation and citalopram on the uptake of serotonin in vivo.

| Group (dosage in mg/kg) | Concentration of serotonin in the brain (mg/kg tissue) | |
|---|---|---|
| | X ± SEM | % in relation to the group after p-chloramphetamine |
| Control | 353 ± 117, 7 (9) | 169 |
| p-CA | 213 ± 19, 7 (10) | 100 |
| Citalopram | | |
| (20) before 6-OHDA | 510 ± 29, 2 (10) | 155 |
| Examined preparation | | |
| (200) before-p-CA | 367 ± 30, 1 (10) | 172 |
| (40) before p-CA | 228 ± 18, 9 (10) | 107 |
| F (4/44 28, 94 ($p < 0, 0001$) | | | p-Chloramphetamine caused a decline of the cerebral serotonine concentration by 40%. Citalopram, applied before p-chloramphetamine, not only prevented the decline of the amine level, but caused its increase over the level of control by 40%. The low dosage of the examined preparation did not produce any effects on the washing-out action of p-chloramphetamine. However, the high dosage prevented the p-chloramphetamine effect completely.

6) The effect on the process of learning and memorising.

The effect was examined on rats by applying the model of learning accompanied by a jump on a bar with or without electroshock. The rats were taught to jump on a bar by means of conditioned (trained) impulse, which was a 1200 Hz frequency sound. The impulse lasted 8 seconds. After this, the rats were treated with electric current at the voltage of 40 V and frequency of 50 Hz for the time of 12 seconds; (unconditioned impulse). Each of the animals received 10 impulse combinations daily in different time intervals (15–30 seconds). The number of conditioned (trained) reactions (jumps on the bar) were measured in the examined and control groups. The preparations (the examined preparation in the dosage of 5 mg/kg, piracetam in the dosage of 100 mg/kg and pyritinol in the dosage of 100 mg/kg) were administered intraperitoneally everyday, 60 minutes before the beginning of the experiment. The control animals received a physiological NaCl solution. It was observed that the examined preparation accelerates the process of learning. The effect is weaker than the effect of piracetam, but stronger than the effect of pyritinol.

7) The effect on the time of survival in the conditions of hypoxia.

Twenty mice, 18–20 g (10 animals were in the control group and 10 were administered the examined preparation) were put into two boxes with nitrogen-flow, whose concentration was being constantly increased (3 l/min). The examined preparation was applied i.o. in the dosages 5, 10, 50, 75, 100 mg/kg 60 minutes before the beginning of the experiment. The experiment lasted until 0–3 animals survived in the control group. Subsequently oxygen was let in and finally normal air. The number of animals which survived in the control group was compared to the number of animals in the group administered the examined preparation. The results are presented in Table 7. The number of surviving mice is presented in relation to the complete number of examined mice.

The results were compared to those of piracetam and pyritinol. It was observed that the examined preparation, in comparison to piracetam and pyritinol, prolongs the time of mice survival in the conditions of hypoxia. Although the test is most frequently applied to the evaluation of nootropic substances, the same effect is demonstrated by preparations of a very different profile of action, among others tranquilisers.

TABLE 7

The number of mice surviving in the conditions of hypoxia

| Preparation | Dosage (mg/kg) | Results | | |
|---|---|---|---|---|
| | | Prepar. | Control | p |
| Examined preparation | 5 | 5/40 | 7/40 | n.d. |
| | 10 | 6/40 | 5/40 | n.d. |
| | 50 | 23/60 | 9/60 | <0, 01 |
| | 75 | 28/60 | 9/60 | <0, 01 |
| | 100 | 47/60 | 9/60 | <0, 01 |
| Piracetam | 100 | 6/40 | 7/40 | n.d. |
| | 300 | 18/60 | 6/60 | <0, 05 |
| Pyritinol | 100 | 30/60 | 8/60 | <0, 01 | n.nd. = not determined

The results of the pharmaceutical examinations give the evidence that the examined preparation has a very complex psychotropic activity, which can be defined as antidepressive with a simultaneous depressive effect on the central nervous system (sedative component). What demonstrates its anti-depressive action is the fact of a very conspicious decline of the beta-adrenergic receptor concentration, which is a characteristic effect of all anti-depressive preparations and procedures. It is also demonstrated by its inhibiting effect on the uptake of noradrenaline or serotonin in vivo. Thirdly, its antidepressive effect is testified by the intensification of L-dopa effects in reserpine pretreated mice and those premedicated with pargyline, as well as by shortening the immobility period in the animal model od depression (rats' depair test).

The intensification of L-dopa effects suggests its anti-depressive and anti-parkinsonian activity. The nootropic characteristic of the examined preparation are demonstrated by its distinctively protecting action in the conditions of hypoxia and by improving the process of learning and memorising.

The examined preparation may prove effective in the therapy of depression combined with hyperpraxia and nervosis with depressive component. Due to its nootropic action it may prove useful in the therapy of elderly.

The composition is presented in more detail in the following examples, which are only illustrative and are not to be construed as limiting the scope of the invention in any way.

EXAMPLE 1. TABLETS

A tablet of the following composition was prepared (in grams):

| | |
|---|---|
| 5 morplolinomethyl-3-(4-chlorobenzylideneamine)-2-oxazolidinone hydrochloride | 0, 05 |
| Avicel (microcrystallic cellulose) | 0, 1073 |
| Ethylcellulose (in the form of 5% anhydrous ethanol solution) | 0, 006 |
| Talc | 0, 005 |
| Magnesium stearate | 0, 0017 |
| | 0, 17 |

EXAMPLE 2. CAPSULES

Hard gelatine capsules were conventionally filled with 5-morpholinomethyl-3-(4-chlorobenzylideneamine)-2-oxazolidinone hydrochloride in such a way that each capsule contained approximately 0,05 g of the active substance.

EXAMPLE 3 DRAGEES

Tablets prepared as in Example 1 were covered in a coating pan with a coat composed of saccharine, potato starch, talc, tragacanth and a coloring agent.

EXAMPLE 4. INJECTIONS

The solution of the following composition was prepared (in grams):

| | |
|---|---|
| 5-morpholinomethyl-3-(4-chlorobenzylideneamine)-2-oxazolidinone hydrochloride | 1 |
| Propylene glycol | 49 |
| Injection water | 50 |
| | 100 |

The solution was sterilised by means of a membrane filter of 0,22 μm pore density and then it was poured into ampoules.

EXAMPLE 5. INJECTIONS

The solution of the following composition was prepared (in grams):

| | |
|---|---|
| 5-morpholinomethyl-3-(4-chlorobenzylideneamine)-2-oxazolidinone hydrochloride | 1 |
| Mannitol | 1 |
| Injection water | 98 |
| | 100 |

The solution was filtered by means of 0,22 μm density pore filter. Subsequently the solution was dosed into ampoules, frozen in the temperature of approximately −30° C. for 15–16 hours and finally freeze-dried for 24 hours. The final temperature was 30° C.

We claim:

1. A pharmaceutical composition comprising a pharmaceutically acceptable carrier, 5-morpholinomethyl-3-(4-chlorobenzylideneamine)-2-oxazolidinone of formula 1

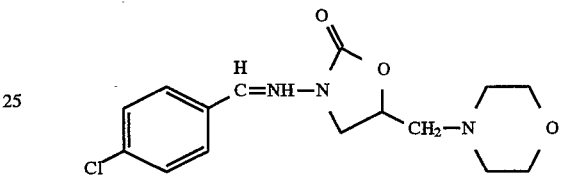

and/or a pharmaceutical acceptable salt of 5-morpholinomethyl-3-(4-chlorobenzylideneamine)-2-oxazolidinone and an auxiliary agent.

2. A pharmaceutical composition comprising a pharmaceutically acceptable carrier selected from the group consisting of water, vegetable oils, benzyl alcohol, polyethylene glycol, gelatine, carbohydrates, magnesium stearate and talc and 5-morpholinomethyl-3-(4-chlorobenzylideneamine)-2-oxazolidinone of formula 1

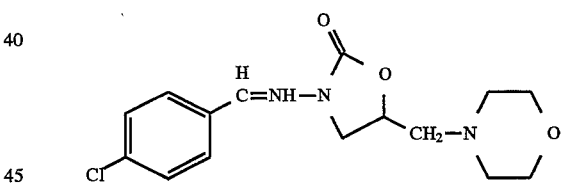

and/or a pharmaceutically acceptable salt of 5-morpholinomethyl-3-(4-chlorobenzylideneamine)-2-oxazolidinone.

3. A pharmaceutical composition as claimed in claim 1, wherein the auxiliary agent is selected from the group consisting of preservatives, stabilizers, buffers, emulsifiers, solubilizers, salts regulating osmotic pressure, binders, lubricants, coloring agents, and flavoring agents.

4. A pharmaceutical composition as claimed in claim 3, wherein the pharmaceutically acceptable carrier is selected from the group consisting of water, vegetable oils, benzyl alcohol, polyethylene glycol, gelatine, carbohydrates, magnesium stearate, and talc.

5. A pharmaceutical composition as claimed in claim 4, wherein the salt is selected from the group consisting of hydrochloric acid salt, hydrobromic acid salt, phosphoric acid salt, formic acid salt, acetic acid salt, propionic acid salt, malonic acid salt, citric acid salt, lactic acid salt, tartaric acid salt, gluconic acid salt, nicotinic acid salt, methanesulphonic acid salt, ethanesulphonic acid salt, ascorbic acid salt, naphthalenesulphonic acid salt, and fumaric acid salt.

6. A pharmaceutical composition comprising a pharmaceutically acceptable carrier and 5-morpholinomethyl-3-(4-chlorobenzylideneamine)-2-oxazolidinone of formula I

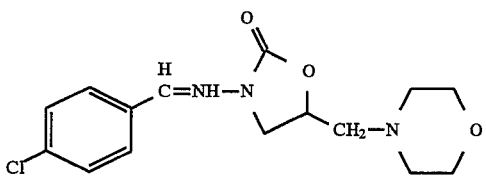

and/or a pharmaceutically acceptable salt of 5-morpholinomethyl-3-(4-chlorobenzylideneamine)-2-oxazolidinone which composition is in the form of a tablet, capsule, powder, granules, syrup, emulsion or suppository.

7. A pharmaceutical composition as claimed in claim 6, wherein the pharmaceutical composition has a form, the form being a tablet.

8. A pharmaceutical composition as claimed in claim 6, wherein the tablet has a parenteral coating.

9. A pharmaceutical composition as claimed in claim 6, wherein the pharmaceutical composition has a form, the form being a capsule.

10. A pharmaceutical composition as claimed in claim 6, wherein the pharmaceutical composition has a form, the form being a powder.

11. A pharmaceutical composition as claimed in claim 6, wherein the pharmaceutical composition has a form, the form being granules.

12. A pharmaceutical composition as claimed in claim 6, wherein the pharmaceutical composition has a form, the form being a syrup.

13. A pharmaceutical composition as claimed in claim 6, wherein the pharmaceutical composition has a form, the form being an emulsion.

14. A pharmaceutical composition as claimed in claim 6, wherein the pharmaceutical composition has a form, the form being a suppository.

15. A method of treating central nervous system diseases and disorders, the diseases and disorders being responsive to drugs possessing psychotropic activity, the method comprising administering to a subject suffering from the disease or disorder a therapeutically effective amount of 5-morpholinomethyl-3-(4-chlorobenzylideneamine)-2-oxazolidinone of formula I and/or a pharmaceutically acceptable salt of 5-morpholinomethyl-3-(4-chlorobenzylideneamine)-2-oxazolidinone.

16. A method as claimed in claim 15, wherein the disease or disorder is depression.

17. A method as claimed in claim 15, wherein the pharmaceutically acceptable salt of 5-morpholinomethyl-3-(4-chlorobenzylideneamine)-2-oxazolidinone is 5-morpholinomethyl-3-(4-chlorobenzylidene-amine)-2-oxazolidinone hydrochloride.

18. A method as claimed in claim 15, wherein the 5-morpholinomethyl-3-(4-chlorobenzylideneamine)-2-oxazolidinone or the pharmaceutically acceptable salt of 5-morpholinomethyl-3-(4-chlorobenzylideneamine)-2-oxazolidinone is administered in a pharmaceutical composition, the pharmaceutical composition further comprising a pharmaceutically acceptable carrier.

19. A method as claimed in claim 18, wherein the pharmaceutical composition further comprises an auxiliary agent.

20. A method as claimed in claim 15, wherein the salt is selected from the group consisting of hydrochloric acid salt, hydrobromic acid salt, phosphoric acid salt, formic acid salt, acetic acid salt, propionic acid salt, malonic acid salt, citric acid salt, lactic acid salt, tartaric acid salt, gluconic acid salt, nicotinic acid salt, methanesulphonic acid salt, ethanesulphonic acid salt, ascorbic acid salt, naphthalenesulphonic acid salt, and fumaric acid salt.

21. A method as claimed in claim 18, wherein the pharmaceutically acceptable carrier is selected from the group consisting of water, vegetable oils, benzyl alcohol, polyethylene glycol, gelatine, carbohydrates, magnesium stearate, and talc.

22. A method as claimed in claim 19, wherein the auxiliary agent is selected from the group consisting of preservatives, stabilizers, buffers, emulsifiers, solubilizers, salts regulating osmotic pressure, binders, lubricants, coloring agents, and flavoring agents.

23. A method as claimed in claim 22, wherein the pharmaceutically acceptable carrier is selected from the group consisting of water, vegetable oils, benzyl alcohol, polyethylene glycol, gelatine, carbohydrates, magnesium stearate, and talc.

24. A method as claimed in claim 23, wherein the salt is selected from the group consisting of hydrochloric acid salt, hydrobromic acid salt, phosphoric acid salt, formic acid salt, acetic acid salt, propionic acid salt, malonic acid salt, citric acid salt, lactic acid salt, tartaric acid salt, gluconic acid salt, nicotinic acid salt, methanesulphonic acid salt, ethanesulphonic acid salt, ascorbic acid salt, naphthalenesulphonic acid salt, and fumaric acid salt.

* * * * *